United States Patent
Nakanishi

[11] Patent Number: 5,868,571
[45] Date of Patent: Feb. 9, 1999

[54] DENTAL HOSE ASSEMBLY

[75] Inventor: Takasuke Nakanishi, Kanuma, Japan

[73] Assignee: Nakanishi Inc., Tochigi-ken, Japan

[21] Appl. No.: 22,662

[22] Filed: Feb. 12, 1998

[30] Foreign Application Priority Data

Feb. 17, 1997 [JP] Japan .............................. 9-000714 U

[51] Int. Cl.⁶ ...................................................... A61C 1/08
[52] U.S. Cl. ........................................... 433/115; 433/126
[58] Field of Search ..................................... 433/126, 115

[56] References Cited

U.S. PATENT DOCUMENTS

| | | | |
|---|---|---|---|
| 3,789,506 | 2/1974 | Johns | 433/126 |
| 4,303,392 | 12/1981 | Rollofson | 433/126 |
| 4,553,938 | 11/1985 | Olsen | 433/126 |
| 5,039,304 | 8/1991 | Heil | 433/126 |
| 5,088,924 | 2/1992 | Woodward | 433/126 |
| 5,145,370 | 9/1992 | Woodward | 433/126 |
| 5,476,379 | 12/1995 | Disel | 433/126 |
| 5,501,596 | 3/1996 | Bailey | 433/126 |

*Primary Examiner*—Jeffrey A. Smith
*Assistant Examiner*—Eduando C. Robert
*Attorney, Agent, or Firm*—Malcolm B. Wittenberg

[57] ABSTRACT

A dental hose assembly for use with a dental handpiece. The assembly comprises inner tubes, an outer tube enclosing the inner tubes, a connector for connecting the inner tubes to fluid passages in the handpiece, a tubular hose guide enclosing the distal ends of the inner tubes, a tubular joint cover engaging the connector and the distal end portion of the outer tube, and a connector ring sheathing the joint cover and to be connected to the handpiece for preventing the connector from being detached from the handpiece. The connector has a proximal end connected to the inner tubes and a distal end to be connected to the dental handpiece. The hose guide has a frustconical portion proximally tapered and distally flared on its outer surface to end with a projected distal end. The distal end portion of the outer tube is fitted over the hose guide to define an expanded portion. The joint cover has a proximal end thickened radially inwardly with a rounded outer edge. The expanded portion of the outer tube is tightly held between the hose guide and the joint cover. The projected distal end of the frustconical portion and the joint cover tightly press the expanded portion therebetween and the expanded portion is fastened distally by the thickened proximal end of the joint cover.

8 Claims, 4 Drawing Sheets

DENTAL HOSE ASSEMBLY

FIELD OF THE INVENTION

The present invention relates to a dental hose assembly for connecting a dental handpiece to a dental unit including fluid supplies for the handpiece, in particular to a dental hose assembly having a structure for connecting to a connector an outer tube which encloses inner tubes for transmitting fluids to a dental handpiece.

PRIOR ART

A dental hose assembly usually has an outer tube enclosing inner tubes such as an air supply tube for transmitting pressurized air for rotationally driving an air turbine in a dental handpiece, an air discharging tube for discharging the used pressurized air, a water supply tube, and a chip air supply tube.

The dental hose assembly is assembled by connecting the inner tubes and the outer tube to a connector. FIG. 7 shows a conventional dental hose assembly. In the drawing, inner tubes 81 are connected to the pipe joints 86' projecting from the proximal end face of the connector 86. Outer tube 85 enclosing the inner tubes 81 is fitted over a thinned proximal portion of joint cover 100 screwed onto connector 86, and expanded a little. Outer guide 90 is then lightly fitted over the expanded portion of outer tube 85, and caulked in the middle, thereby fixing and securely connecting the outer tube 85 to the connector 86. The caulking of the outer guide 90 is effected by squashing the outer surface of the guide 90 inward between slits provided in parallel on the guide 90 at regular circumferential intervals. If the caulking is not sufficient, the outer tube 85 is easily detached from the joint cover 100 during use.

The dental hose assembly thus assembled is then connected to a handpiece by connecting the connector 86 to the proximal end of the handpiece, sheathing the connector 86 by connector ring (FIG. 1), and screwing the connector ring onto the proximal end of the handpiece.

However, since the conventional dental hose assembly requires caulking process, connection of the outer tube is not easy. Further, the outer tube, once connected by the caulking process, can hardly be disconnected or re-connected. Therefore, the distal end portion of the dental hose assembly cannot be disassembled for cleaning the distal ends of the inner tubes.

The conventional dental hose assembly has another problem in that when the outer tube is bent or twisted during use, portion of the outer tube which comes into contact with the thin edge of the outer guide is easily damaged and worn out.

SUMMARY OF THE PRESENT INVENTION

It is an object of the present invention to provide a dental hose assembly which requires no caulking process in assembling, in which the outer tube is easily and securely fixed and hardly detached accidentally, and in which the outer tube is not damaged and worn out.

According to the present invention, there is provided a dental hose assembly for use with a dental handpiece having a proximal end and a plurality of fluid passages, said assembly comprising:

a plurality of inner tubes each having a distal end;

an outer tube having a distal end portion and enclosing said inner tubes;

a connector for connecting the inner tubes to the fluid passages in the handpiece, said connector having an outer surface, a proximal end connected to the distal ends of the inner tubes, and a distal end to be connected to the proximal end of the dental handpiece;

a tubular hose guide having an outer surface and a proximal end and enclosing the distal ends of the inner tubes, said hose guide having a frustconical portion proximally tapered on the outer surface to reduce thickness of the proximal end of the hose guide and distally flared on the outer surface to end with a projected distal end in the middle of the hose guide, said distal end portion of said outer tube being fitted over the hose guide to define an expanded portion having a proximal end;

a tubular joint cover engaging the outer surface of the connector and the distal end portion of the outer tube, said joint cover having a proximal end thickened radially inwardly, said thickened proximal end having a rounded outer edge; and a connector ring sheathing said joint cover and to be connected to the proximal end of the handpiece for preventing said connector from being detached from the handpiece;

wherein said expanded portion of said outer tube is tightly held between the hose guide and the joint cover, said projected distal end of the frustconical portion of the hose guide and the joint cover tightly pressing the expanded portion of the outer tube therebetween, and wherein said proximal end of the expanded portion of the outer tube is fastened distally by the thickened proximal end of the joint cover.

In the dental hose assembly of the present invention, the distal end portion of the outer tube is held between a hose guide placed inside the outer tube and a joint cover placed around the outer tube to thereby connect and fix the outer tube to a connector. The hose guide has a frustconical portion tapered proximally to facilitate fitting of the distal end portion of the outer tube thereon and flared distally to end with a projected distal end. The distal end portion of the outer tube is fitted over the hose guide and expanded to form an expanded portion having a lager diameter, and a part of the expanded portion is further expanded by the projected distal end of the frustconical portion of the hose guide.

The frustconical portion of the hose guide may be tapered and flared at an angle of 5° to 15°. If the angle is less than 5°, the height of the projected proximal end of the frustconical portion is not sufficient to catch the outer tube. If the angle exceeds 15°, fitting of the outer tube over the frustconical portion becomes difficult. Therefore, the tapering and flaring angle is preferably about 10°.

The hose guide may additionally be provided with an annular groove on its outer surface disposed distally adjacent to the projected distal end of the frustconical portion. Due to the annular groove, the difference in level of the projected distal end 23 sharpens to broaden the distal end face of the frustconical portion, thereby ensuring holding of the distal end portion of the outer tube between the joint cover and the projected proximal end of the frustconical portion, and improving the resistance to the displacement of the outer tube in the detaching direction.

The joint cover engages the connector and tightly holds the expanded portion of the outer tube without any substantial gaps therebetween, and presses radially inwardly the expanded portion of the outer tube over the projected distal end of the frustconical portion of the hose guide, thereby securely pressing the outer tube between the joint cover and the hose guide.

According to the present invention, connection between the joint cover and the connector is made by means of press-fitting and detent means, which facilitates assembly of the hose assembly. It is preferred that the detent means includes an axial channel on the outer surface of the connector and a boss on the inner surface of the joint cover for engagement within the axial channel.

Further, with the joint cover engaging the connector, the thickened proximal end of the joint cover distally fastens the proximal end of the expanded portion of the outer tube to resist the proximal displacement of the outer tube. In this state, the clearance between the inner edge of the thickened proximal end of the cover and the proximal end of the hose guide is generally equal to the thickness of the outer tube. The outer edge of the thickened proximal end of the joint cover is rounded so as not to damage the outer tube portion which comes into contact with the outer edge of the thickened proximal end when the outer tube is bent or twisted in use. Therefore, the outer tube is not susceptible to wearing.

The thickened proximal end of the joint cover may be slightly rounded also at the inner edge thereof which contacts and distally fastens the proximal end of the expanded portion of the outer tube. Due to this configuration, the outer tube portion which comes into contact with the inner edge of the thickened proximal end will not be damaged to wear.

A connector ring which sheathes the joint cover and is screwed to the handpiece ensures connection between the joint cover and the connector for preventing displacement of the joint cover relative to the connector. Accordingly, when the dental hose assembly is connected to a dental handpiece, the connector ring restrains the joint cover to prevent the cover from being detached.

In the present invention, the inner tubes may include an air supply tube, an air discharging tube, a water supply tube, and a chip air supply tube, and the dental handpiece may be provided with an air turbine.

EXAMPLES

The dental hose assembly of the present invention will now be explained in more detail with reference to the Examples and the attached drawings.

Figure 1:
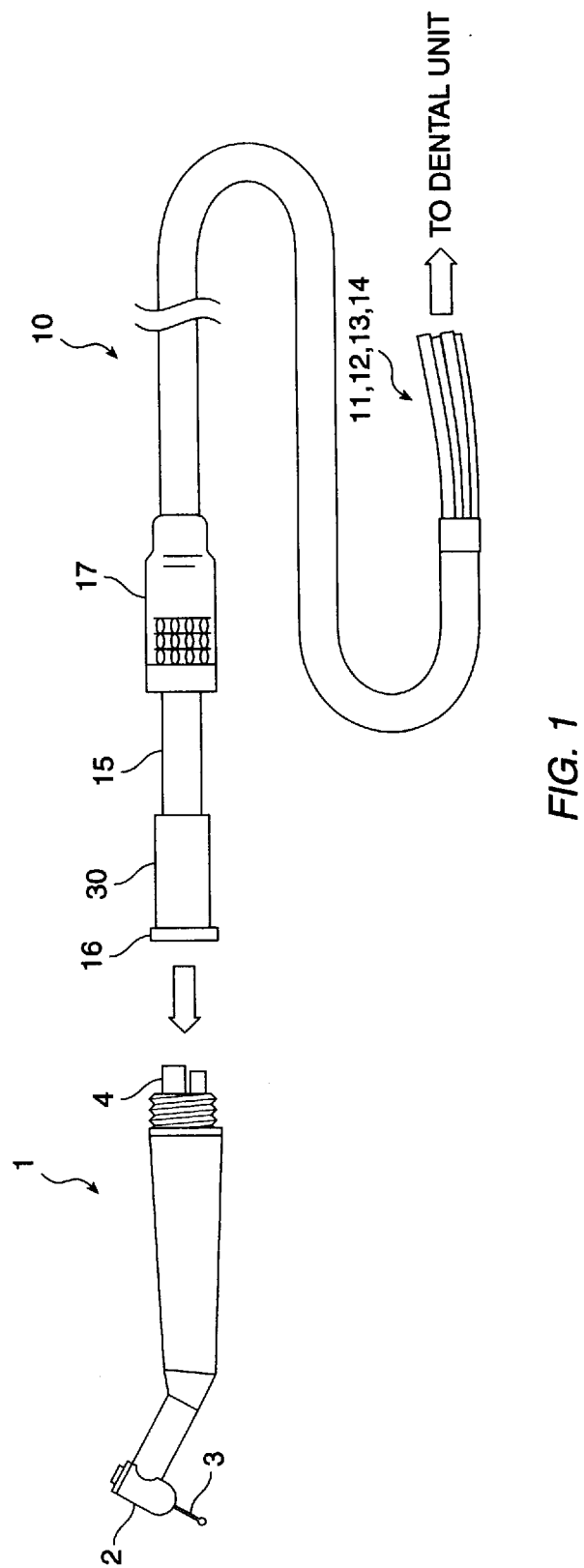
FIG. 1 is a schematic explanatory view of a dental handpiece and a dental hose assembly of the present invention.
Figure 2:
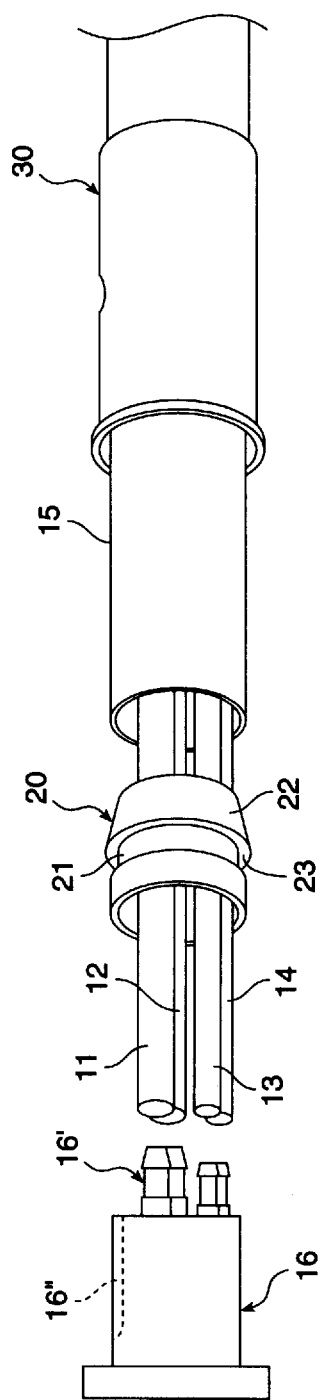
FIG. 2 is an exploded perspective view of the distal end portion of a dental hose assembly of the present invention, with a connector ring being eliminated for the sake of clarity.

FIG. 1 is a schematic explanatory view of dental handpiece 1 and dental hose assembly 10 of the present invention to be connected to the handpiece 1 at the distal end thereof. The detail of the distal end portion of the dental hose assembly 10 is shown in an exploded perspective view in FIG. 2, and in a cross-sectional view in FIG. 3, with the connector ring 17 being eliminated for the sake of clarity. The proximal end of the dental hose assembly 10 is connected to a dental unit (not shown) in a conventional manner.

The dental handpiece 1 has head 2 accommodating an air turbine (not shown) for rotationally driving dental tool 3, and encloses fluid passages. The fluid passages include an air supply passage for transmitting pressurized air for rotationally driving the air turbine from the dental unit, a water supply passage for transmitting cooling water for cooling the treatment site, a chip air supply passage for transmitting chip air for blowing off the debris, and an air discharging passage for discharging the pressurized air used for driving the air turbine. Proximal ends 4 of the fluid passages are shown exposed out of the handpiece 1 in FIG. 1.

The dental hose assembly 10 accommodates inner tubes including an air supply tube 11, an air discharging tube 12, a water supply tube 13, and a chip air supply tube 14, each to be connected to the corresponding fluid passages in the handpiece 1. The diameter of the air supply tube 11 and the air discharging tube 12 is larger than the diameter of the water supply tube 13 and the chip air supply tube 14, and the same is true for the corresponding fluid passages in the handpiece 1. The inner tubes, as well as lead wires (not shown) for electrical connection, are enclosed in outer tube 15 having a smooth surface coated with silicon.

Before connected to the handpiece 1, the dental hose assembly 10 is assembled by connecting the inner tubes 11, 12, 13, 14 and the outer tube 15 to connector 16 made of a hard resin. Specifically, the distal ends of the inner tubes 11, 12, 13, 14 are connected to the pipe joints 16' projecting from the proximal end of the connector 16, and the outer tube 15 is fitted over the outer surface of hose guide 20 made of a soft resin, which is placed adjacent to the proximal end of the connector 16. Then, the connector 16 and the hose guide 20 having the distal end portion of the outer tube 15 fitted on its outer surface are sheathed by a joint cover 30 made of brass to securely fixing the outer tube 15 to the connector 16, thereby completing the assembly.

Figure 4:
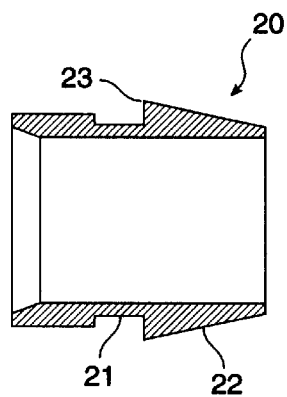
FIG. 4 is a sectional view of a hose guide.

Referring to FIG. 4, the hose guide 20 is a generally tubular member of which inner diameter is almost the same as the inner diameter of the outer tube 15. The hose guide 20 has a frustconical portion 22 tapered proximally at 10° for reducing the outer diameter of the hose guide 20 toward the proximal end thereof. That is, the frustconical portion 22 reduces the thickness of the guide 20 in the proximal end portion thereof. The frustconical portion 22 is also flared distally at 10° to end with projected distal end 23 which has the largest outer diameter in the guide 20 and projects radially outwardly from the outer surface of the guide 20. The hose guide 20 is further provided with an annular groove 21 on its outer surface disposed distally adjacent to the projected distal end 23 of the frustconical portion 22 and in the middle of the length of the hose guide 20. The portion of the guide 20 distal to the groove 21 has uniform thickness with the outer diameter being approximately equal to the original outer diameter of the outer tube 15 before expansion.

Figure 3:
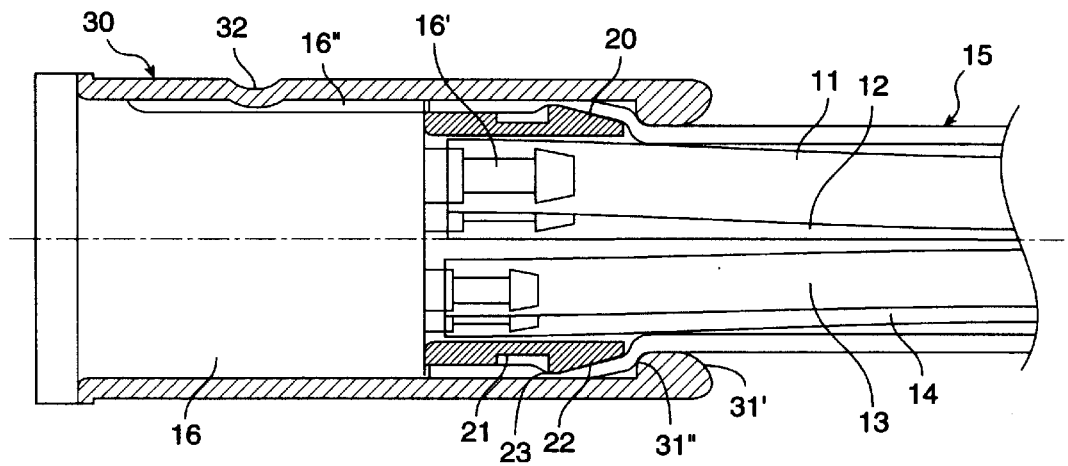
FIG. 3 is a sectional view of the distal end portion of a dental hose assembly of the present invention in the assembled state, with a connector ring being eliminated for the sake of clarity.

Referring to FIG. 3, the joint cover 30 is a generally tubular member having the inner diameter approximately equal to the outer diameter of the connector 16. By designing the inner diameter of the cover 30 to generally conform to the outer diameter of the connector 16, the distal half of the cover 30 is press-fitted over the connector 16 to ensure the connection between the two parts. In this connected state, boss 32 on the inner surface of the joint cover 30 engages in axial channel 16" in the outer surface of the connector 16 to prevent rotational movement of the cover 30 around the connector 16. Further, after press-fitting the cover 30 over the connector 16, the cover 30 may be fixed to the connector 16 by inserting a pin (not shown) through the cover into the connector.

Figure 5:
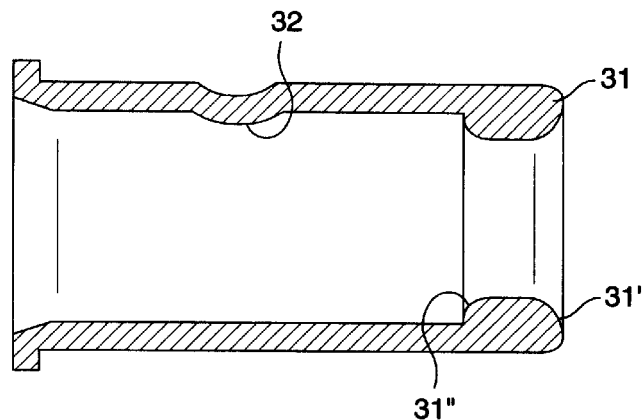
FIG. 5 is a sectional view of a joint cover.

Referring to FIG. 5, the joint cover 30 has a thickened proximal end 31 which is projected radially inwardly to form an annular step. The outer edge 31' of the thickened proximal end 31 is rounded with a larger radius of curvature, while the inner edge 31" of the thickened proximal end 31 forming a step is rounded with a smaller radius of curvature.

Figure 6:
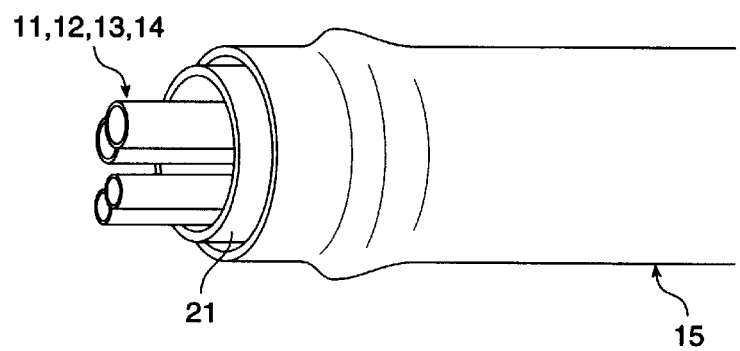
FIG. 6 is a perspective view showing an outer tube fitted over a hose guide.
Figure 7:
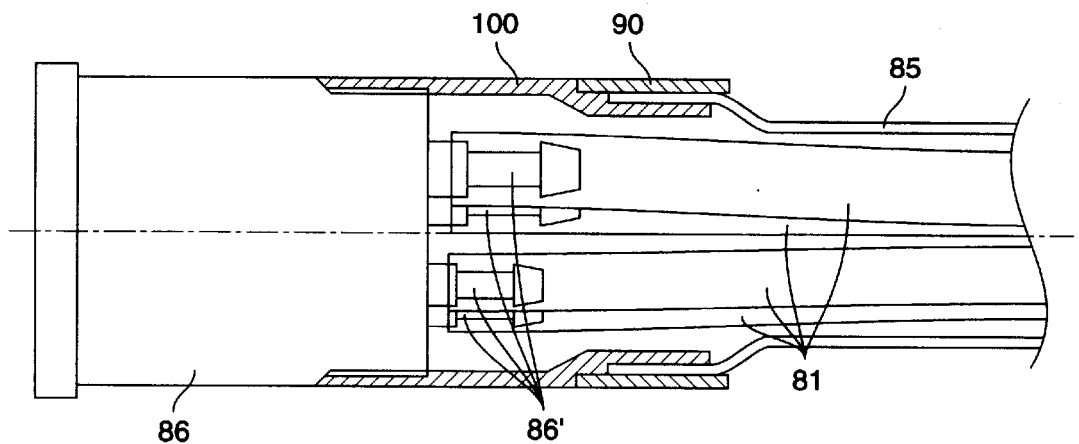
FIG. 7 is a sectional view of the distal end portion of a conventional dental hose assembly in the assembled state.

The distal portion of the dental hose assembly 10 may be assembled in the following way. First, the inner tubes 11, 12, 13, 14 are connected to the pipe joints 16' projecting from the proximal end of the connector 16. Next, the hose guide 20 is slid distally until the distal end of the guide 20 abuts the proximal end of the connector 16 to cover the distal ends of the inner tubes 11, 12, 13, 14 connected to the pipe joints 16'. Then the distal end portion of the outer tube 15 is fitted over the outer surface of the hose guide 20 from its tapered end of the frustconical portion 22. The frustconical portion 22 of the hose guide 20 facilitates this fitting process. The distal end portion of the outer tube 15 covering the hose guide 20 is thus expanded to have an enlarged diameter, with the tube portion over the projected distal end 23 of the frustconical portion 22 of the hose guide 20 being projected radially outwardly the most with the largest diameter as shown in FIG. 6.

Subsequently, the joint cover 30 is slid distally until the distal half of the cover 30 is press-fitted over the outer surface of the connector 16, thereby completing the assembly.

In this assembled state as shown in FIG. 3, the inner surface of the proximal half of the cover 30 presses radially inwardly the expanded portion of the outer tube over the projected distal end 23 of the frustconical portion 22 of the hose guide 20. As a reaction, the outer tube portion elastically resists the pressure to impose radially outward force to the cover 30. These action and reaction reinforce the press-fit connection between the cover 30 and the connector 16. The distal portion of the outer tube 15 is thus closely pressed and securely held between the proximal half of the cover 30 and the hose guide 20 substantially without any gap.

Further, the thickened proximal end 31 of the cover 30 imposes distally fastening force to the proximal end of the expanded portion of the outer tube 15 to provide additional support. The inner edge 31" of the thickened proximal end 31 and the proximal end of the frustconical portion 22 of the guide 20 define a clearance which is equal to or slightly larger than the thickness of the outer tube 15. Due to the clearance of this size, the thickened proximal end 31 sufficiently fastens the proximal end of the expanded portion of the outer tube without applying too much load thereto which may cause wearing of the outer tube.

When a proximal force for detaching the outer tube 15 from the connector 16 is applied during use, the pressure applied to the distal end portion of the outer tube 15 by the proximal half of the cover 30, the distally fastening force applied to the proximal end of the expanded portion of the outer tube 15 by the thickened proximal end 31 of the cover 30, as well as the convex-concave configuration of the expanded portion of the outer tube 15 corresponding to the annular groove 21 and the projected distal end 23 of the frustconical portion 22 of the hose guide 20, resist the proximal displacement of the outer tube 15. Therefore, the outer tube 15 will never be pulled out accidentally. Further, since the outer edge 31' of the thickened proximal end 31 of the joint cover 30 is rounded, the portion of the outer tube 15 which comes into contact with the outer edge 31' is not worn easily even if the outer tube 15 is bent or twisted during use.

For connecting the dental hose assembly 10 assembled as described above to a dental handpiece 1, first the ports (not shown) provided at the distal end face of the connector 16 which respectively communicate with the joints 16' are fitted to the proximal ends 4 (FIG. 1) of the fluid passages projecting from the proximal end of the handpiece 1. Accordingly, the inner tubes 11, 12, 13, 14 are brought into fluid communication with the fluid passages in the handpiece 1 in gas and water tight manner. Next, connector ring 17 (FIG. 1) is slid distally to cover the joint cover 30 and screwed onto the proximal end of the handpiece 1, thereby accomplishing the connection of the dental hose assembly 10 to the handpiece 1. In this state, the connector ring 17 prevent the connector 16 from being detached from the handpiece 1 and prevent the joint cover 30 from displacing proximally, i.e. from being detached from the connector 16.

With the dental hose assembly of the present invention, the distal end portion of the outer tube is fitted over the hose guide, and then sheathed by a joint cover which is press-fitted over the connector. Thus, the distal end portion of the outer tube is securely held between the hose guide and the joint cover, and the proximal end of the expanded portion of the outer tube is distally fastened by the thickened proximal end of the joint cover. Therefore, connection and fixation of the outer tube are easily and securely achieved without the conventional caulking operation.

Further, the stepped projection on the hose guide resists the detaching displacement of the outer tube, which also ensures the firm fixation of the outer tube.

Due to the thickened proximal end of the joint cover with the rounded outer edge, the outer tube portion which comes into contact with the edge during use is not damaged and worn.

Further, elimination of the caulking operation enables disassembling and re-assembling of the dental hose assembly, which improves the facility in maintenance.

Since the joint cover is press-fitted over the connector, the dental hose assembly is easily assembled.

Although the present invention has been described with reference to the preferred embodiment, it should be understood that various modifications and variations can be easily made by those skilled in the art without departing from the spirit of the invention.

Accordingly, the foregoing disclosure should be interpreted as illustrative only and is not to be interpreted in a limiting sense. The present invention is limited only by the scope of the following claims.

What is claimed is:

1. A dental hose assembly for use with a dental handpiece having a proximal end and a plurality of fluid passages, said assembly comprising:

a plurality of inner tubes each having a distal end;

an outer tube having a distal end portion and enclosing said inner tubes;

a connector for connecting the inner tubes to the fluid passages in the handpiece, said connector having an outer surface, a proximal end connected to the distal ends of the inner tubes, and a distal end to be connected to the proximal end of the dental handpiece;

a tubular hose guide having an outer surface and a proximal end and enclosing the distal ends of the inner tubes, said hose guide having a frustconical portion proximally tapered on the outer surface to reduce thickness of the proximal end of the hose guide and distally flared on the outer surface to end with a projected distal end in a middle of the hose guide, said distal end portion of said outer tube being fitted over the hose guide to define an expanded portion having a proximal end;

a tubular joint cover engaging the outer surface of the connector and the distal end portion of the outer tube, said joint cover having a proximal end thickened radially inwardly, said thickened proximal end having a rounded outer edge; and a connector ring sheathing said joint cover and to be connected to the proximal end of the handpiece for preventing said connector from being detached from the handpiece;

wherein said expanded portion of said outer tube is tightly held between the hose guide and the joint cover, said projected distal end of the frustconical portion of the hose guide and the joint cover tightly pressing the expanded portion of the outer tube therebetween, and wherein said proximal end of the expanded portion of the outer tube is fastened distally by the thickened proximal end of the joint cover.

2. The dental hose assembly as claimed in claim 1 wherein said joint cover engages the outer surface of the connector by means of press-fitting and detent means.

3. The dental hose assembly as claimed in claim 2 wherein said joint cover has an inner surface, and wherein said detent means comprises an axial channel on the outer surface of the connector and a boss on the inner surface of the joint cover for engaging in the axial groove.

4. The dental hose assembly as claimed in claim 1 wherein said hose guide further comprises an annular groove on its outer surface disposed distally adjacent to the projected distal end of the frustconical portion.

5. The dental hose assembly as claimed in claim 1 wherein said frustconical portion is tapered and flared at an angle of 5° to 15°.

6. The dental hose assembly as claimed in claim 1 wherein said thickened proximal end of the joint cover has a rounded inner edge.

7. The dental hose assembly as claimed in claim 1 wherein said connector ring prevents the joint cover from displacing with respect to the connector when the connector ring is connected to the proximal end of the handpiece.

8. The dental hose assembly as claimed in claim 1 wherein said inner tubes comprise an air supply tube, an air discharging tube, a water supply tube, and a chip air supply tube.

* * * * *

UNITED STATES PATENT AND TRADEMARK OFFICE
CERTIFICATE OF CORRECTION

PATENT NO. : 5,868,571
DATED : February 9, 1999
INVENTOR(S) : Takasuke Nakanishi It is certified that error appears in the above-identified patent and that said Letters Patent is hereby corrected as shown below:

Drawings:

In FIG. 6, delete reference numeral "21" and insert therefor --20--.

Signed and Sealed this

Twenty-seventh Day of June, 2000

Attest:

Q. TODD DICKINSON

Attesting Officer

Director of Patents and Trademarks